(12) United States Patent
Kikuchi et al.

(10) Patent No.: US 7,998,710 B2
(45) Date of Patent: Aug. 16, 2011

(54) PROCESS FOR PURIFYING DIFRUCTOSE DIANHYDRIDE III

(75) Inventors: Hiroto Kikuchi, Hokkaido (JP); Hiroaki Sakurai, Hokkaido (JP); Norimitsu Takagi, Hokkaido (JP); Tsutomu Aritsuka, Hokkaido (JP); Yoshihiro Senba, Hokkaido (JP); Fusao Tomita, Hokkaido (JP); Kozo Asano, Hokkaido (JP)

(73) Assignee: Nippon Beet Sugar Mfg., Co., Ltd., Tokyo (JP)

( * ) Notice: Subject to any disclaimer, the term of this patent is extended or adjusted under 35 U.S.C. 154(b) by 382 days.

(21) Appl. No.: 10/516,307

(22) PCT Filed: Mar. 2, 2004

(86) PCT No.: PCT/JP2004/002592
§ 371 (c)(1),
(2), (4) Date: Dec. 10, 2004

(87) PCT Pub. No.: WO2004/078989
PCT Pub. Date: Sep. 16, 2004

(65) Prior Publication Data
US 2006/0051845 A1 Mar. 9, 2006

(30) Foreign Application Priority Data
Mar. 5, 2003 (JP) .................................. 2003-58929

(51) Int. Cl.
*C12P 19/12* (2006.01)
*C12P 1/00* (2006.01)
*C12P 1/02* (2006.01)
*C12P 19/44* (2006.01)
*B01D 15/04* (2006.01)

(52) U.S. Cl. ............ 435/100; 435/72; 435/74; 435/171; 210/656; 210/694

(58) Field of Classification Search ...................... None
See application file for complete search history.

(56) References Cited

U.S. PATENT DOCUMENTS
5,057,418 A * 10/1991 Uchiyama et al. .............. 435/99
7,487,283 B2 * 2/2009 Sivertsen ...................... 710/306

FOREIGN PATENT DOCUMENTS

| | | | |
|---|---|---|---|
| JP | 49-117688 | | 11/1974 |
| JP | 49117688 A | * | 11/1974 |
| JP | 2-115193 | | 4/1990 |
| JP | 1-285195 | | 11/1990 |
| JP | 3-259090 | | 11/1991 |
| JP | 03259090 A | * | 11/1991 |
| JP | 4-271792 | | 9/1992 |
| JP | 5-168419 | | 7/1993 |
| JP | 11-43438 | | 2/1999 |
| JP | 11-103814 A | | 4/1999 |
| JP | 2002-017391 A | | 1/2002 |
| JP | 2004-305125 A | | 11/2004 |

OTHER PUBLICATIONS

Armarego, W.L.F. and Perrin, D.D. "Common Physical Techniques Used in Purification", Purification of Laboratory Chemicals, 4th Ed., 1996, chapter 1, pp. 1-3 and 12-27.*
Hiroto Kikuchi, et al. "Physical, Chemical and Physiological Properties of Difructose Anhydride III Produced from Inulin by Enzymatic Reaction." Journal of Applied Glycoscience (2004), 51(4), 291-296.*
Katsuichi Saito and Fusao Tomita "Difructose Anhydrides: Their Mass-Production and Physiological Functions" Biosci. Biotechnol. Biochem. 2000, 64(7), 1321-1327.*
Nat'l. Drinking Water Clearinghouse (NDWC) "Organic Removal" NDWC Tech Brief, Aug. 1997, 4 pages.*
Armenante, P.M., "Adsorption" New Jersey Institute of Technology (NJIT) <http://cpe.njit.edu/dlnotes/CHE685/Cls11-1.pdf> archived Feb. 1, 2001 (accessed online Oct. 18, 2010), 65 pages.*
USACE "Engineering and Design: Adsorption Design Guide" Design Guide DG 1110-1-2, Mar. 1, 2001, 99 pages.*
Eiichi, Shirasawa et al., "Preparation of Di-D-fructofuranose 1,2' :2,3' dianhydride by the Cultivation of Arthrobacter ureafaclens in the Inulin-containing Synthetic and Vegetable Media", J.Ferment. Technol., vol. 52, No. 3, pp. 164 to 170, 1974.
Ulrich, Jahnz, et al., "Effective development of a biotechnical process: Screening, genetic engineering, and immobilization for the enzymatic conversion of inulin to DFA III on industrial scale", Landbauforschung Voelkenrode, vol. 518, No. 3, pp. 131 to 136, 2001.
Atsushi, Yokota et al., "Production of Inulin Fructotransferase (Depolymerizing) by *Arthrobacter* sp. H65-7 and Preparation of DFA III from Inulin by the Enzyme", J.Fermentl Bioeng., vol. 72, No. 4, pp. 258 to 261, 1991.
U.S. Appl. No. 11/722,936, filed Jun. 27, 2007, Nagura, et al.
"Brix", Wikipedia. Wikimedia Foundation, Inc. Online Jul. 17, 2008. [retrieved on Sep. 4, 2008]. Retrieved from the Internet <http://en.wikipedia.org/wiki/Brix>, 3 pages.
Hondo Masaaki, et al., "Effects of activated carbon powder treatment on clarificaiton, decolorization, deodorization and fructooligosaccharide content of yacon juice", J. Soc. Food. Sci. Technol., 2000, vol. 47, pp. 148-154 (Abstract).
Potwora, R. J., et al., "Powdered activated carbons: a new generation for sugar refining", International Sugar Journal, vol. 100, No. 1190, pp. 76-79, Feb. 1998 (Abstract).

* cited by examiner

*Primary Examiner* — Chris R Tate
*Assistant Examiner* — Aaron Kosar
(74) *Attorney, Agent, or Firm* — Oblon, Spivak, McClelland, Maier & Neustadt, L.L.P.

(57) ABSTRACT

In the invention, highly pure crystals of difructose dianhydride III (di-D-fructofuranose-1,2':2,3'-dianhydride; hereinafter referred to as DFA III) are produced by adding 5% or less of powdered active carbon to a DFA III containing purified solution containing DFA III of 90% or more purity at a concentration of R-Bx 10-60, preferably 40-55, and after stirring, applying the mixture to solid-liquid separation (filtration with diatomaceous, filtration through a membrane filter, ultrafiltration, or continuous centrifugal separation) and concentrating the separated liquid part, followed by immediate crystallization.
In the process of the invention, DFA III crystals can be produced efficiently and industrially, and the resulting crystals can be used for various purposes in pharmaceuticals or food and drink since they have no smell. This is characteristics of the invention different from the prior art products.

21 Claims, 4 Drawing Sheets

PROCESS FOR PURIFYING DIFRUCTOSE DIANHYDRIDE III

TECHNICAL FIELD TO WHICH THE INVENTION PERTAINS

The present invention relates to a process for purifying difructose dianhydride III ($\alpha$-D-fructofuranose-$\beta$-D-fructofuranose-2',1:2,3'-dianhydride) (hereinafter sometimes referred to as DFA III). More particularly, it relates to an industrially applicable and highly effective process for obtaining highly purified crystals of DFA III from a DFA III solution without repeating recrystallization many times, the crystals having no smell as a result of purification.

PRIOR ART

Difructose dianhydride III (DFA III) is a practically indigestible disaccharide in which 2 molecules of fructose is binding at the 1,2':2,3' positions (i.e., di-D-fructofuranose-1,2';2,3' dianhydride). DFA III is highly soluble in water, of which the solubility is approximately 90-95% compared with that of sucrose, and the sweetness about 52% of sucrose.

Recently, it has been elucidated by the researchers involved in the present applicant that DFA III has an effect of promoting the absorption of minerals such as Ca (see, for example, Patent Document 1), and accordingly DFA III is expected to be a useful material in pharmaceuticals, health foods, certain foods for good health, and other food and drink, particularly for aged people and infants. Thus, it has been long sought to be developed a process for producing highly pure, easily treatable and processing crystals of DFA III on a large scale and low cost differing from a small scale and high cost as in laboratory reagents.

Up to now, DFA III has been prepared as follows: a bacterium or an enzyme fructosyltrasferase, i.e., inulin fructotransferase produced by a bacterium, is allowed to act on inulin or an inulin-containing material (e.g., an extract of Jerusalem artichoke, burdock or chicory) to yield a solution containing DFA III, which is further processed to yield a solution rich in DFA III.

For example, the following process has been proposed; a DFA III containing solution is passed through a column of active carbon, by which DFA III is adsorbed; the column is eluted with ethanol to recover a fraction rich in DFA III, which is evaporated to dryness (e.g., see Patent Documents 2 and 3). This process is, however, a laboratory-scale process for recovery, and accordingly it is hard to consider it as an industrially applicable process for large-scale production. In another process for purification, a solution which is prepared by the above-mentioned enzymatic reaction is purified by an ion-exchange resin, followed by evaporation to dryness (e.g., see Patent Document 4); in this process, however, the purity of DFA III is low, and it is hard to consider it as a process for producing highly pure crystals of DFA III. In addition, the DFA III crystals crystallized in the prior art has a smell which cannot be eliminated by crystallization though other impurities can be eliminated. This residual smell was an unavoidable disadvantage. Though this smell can roughly be eliminated by repetition of recrystallization, the recrystallization has to be repeated many times, and results in decrease of a yield rate every operation. This recrystallization process cannot be applied on an industrial scale.

Thus, there is no successful report on odorless and highly pure crystals of DFA III produced on an industrial and large scale.
Patent Document 1
  JP-A 11-43438
Patent Document 2
  JP-B 56-26400
Patent Document 3
  JP-A 3-259090
Patent Document 4
  JP-A 1-285195

PROBLEM TO BE SOLVED BY THE INVENTION

As mentioned above, in recent years, there is an increasing demand for DFA III as valuable use of DFA III is developed. Thus, it has been demanded to provide highly pure DFA III crystals from which saccharides and various impurities other than DFA III have been eliminated when DFA III is used not only as pharmaceuticals but also as food and drink. Particularly, among these impurities, it has been demanded that no smell as well as color remains in the crystals. In the prior art, however, it was extremely difficult to eliminate a smell from the DFA III crystals and it was impossible to produce highly purified and crystallized DFA III from which even the smell was eliminated without repetition of crystallization efficiently and industrially on a large scale. Thus, it has been demanded to solve these problems in this industry.

MEANS FOR SOLVING PROBLEM

As mentioned above, the smell of DFA III could not be eliminated by a conventional crystallization method in the prior art (in other words, a smell remains after crystallization). Contrary, the process of the invention makes it possible first time to successfully produce DFA III with no smell efficiently and industrially on a large scale.

That is, the present inventors found for the first time as a result of a many-faceted attack on the problem that highly pure DFA III crystals of which the purity reaches 95% or more, specifically 95-99%, can be obtained very efficiently, not by passing a DFA III solution through a column of granular active carbon, but by adding a small amount of powdered active carbon to a DFA III solution, stirring the latter, and applying the latter to filtration with diatomaceous earth filtration and subsequent filtration through a membrane filter, followed by solid-liquid separation, concentration and crystallization of the liquid condensate. It was also found, in the course of this study, that the DFA III fraction obtained by chromatography of a DFA III containing solution can be subjected to direct crystallization after addition of powdered active carbon and subsequent solid-liquid separation and that the crystals thus recovered have no smell.

The present invention was completed as a result of further studies based on the above valuable new findings. In this invention, the inventors have succeeded for the first time in developing a process for large scale production of highly pure DFA III crystals or their granules with no smell though it could not be attained in the prior art. Thus, the process of the invention makes it possible to carry out purification and crystallization of very expensive DFA III at low costs, and it is unnecessary to repeat recrystallization many times, which operation was carried out only occasionally on a laboratory scale to eliminate a smell in the prior art.

Figure 1:
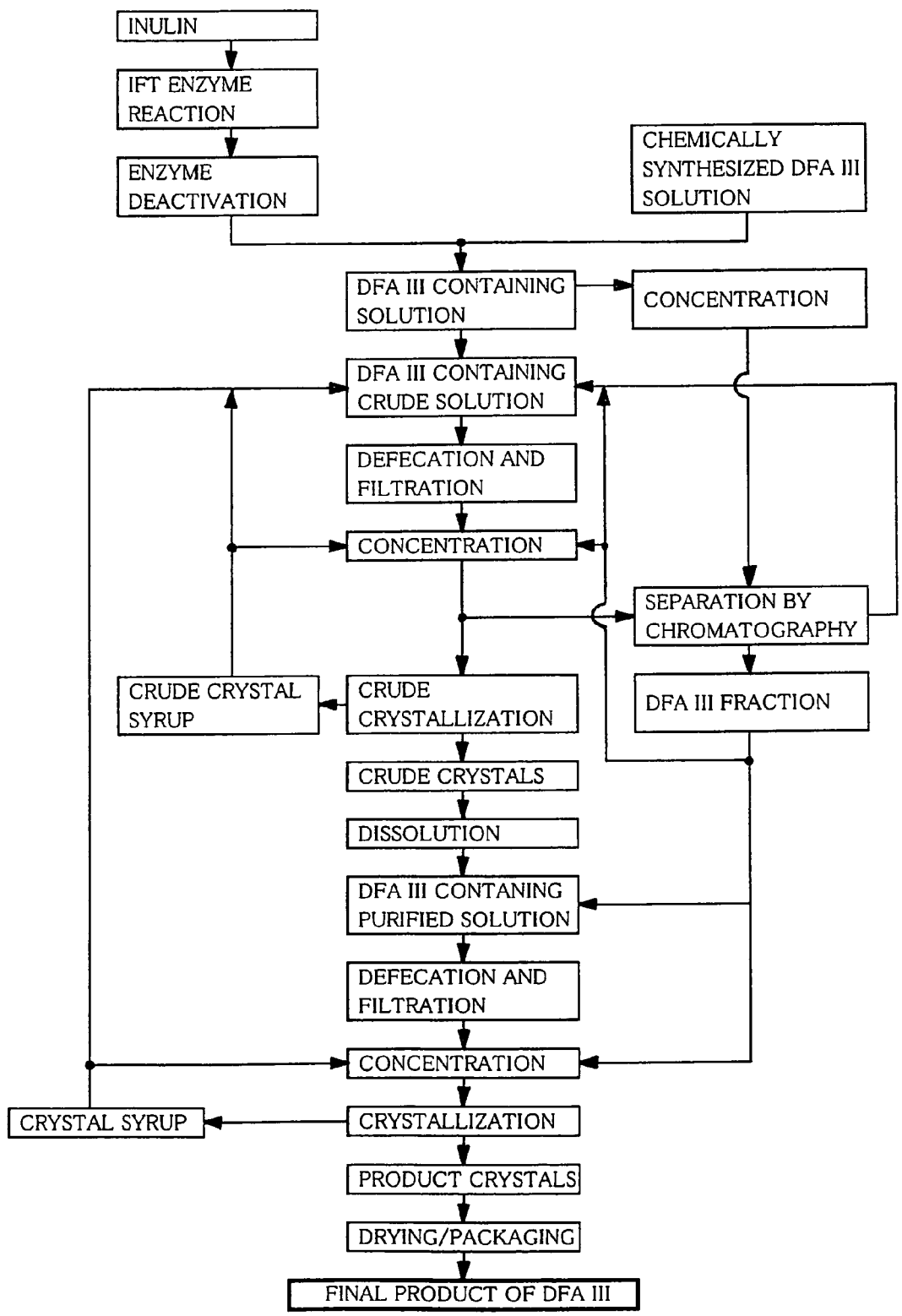
FIG. 1 shows an example of a flow chart illustrating the production of DFA crystals.

The invention will be explained in detail as follows:

In the invention, a DFA III containing solution is purified to produce highly pure DFA III crystals efficiently on an industrial scale. The DFA III containing solution includes all of liquid materials containing DFA III and satisfying the terms as mentioned below, i.e., a DFA III-producing solution prepared by allowing a fructosyltrasferase to act on inulin or a solution containing inulin, as well as a solution obtained by chemical synthesis of DFA III or a solution containing DFA III of diverse degrees of purity generated during the course of purification of the invention.

For example, when DFA III is produced from inulin (and/or a solution containing inulin) and an enzyme, inulin which is generated by polymerization of a number of fructose is used as an extract mainly from chicory (or Jerusalem artichoke, burdock, etc.); commercially available products of inulin, however, are diverse in their polymerization degree and purity, and when they are degraded with an enzyme, the product reaction mixture unavoidably contains fructose polymers other than DFA III, together with enzyme, microorganism used as an enzyme source, its culture medium, pigment, smell, etc., as impurities. In the prior art, accordingly, pure DFA III crystals or a product containing them cannot been produced efficiently at low cost on an industrial scale.

As for a method for purifying an enzyme reaction mixture, as described above, a method of using an ion-exchange resin or an active carbon column has been known (Patent Documents 4 and 2, 3); in these methods, however, treatment and operation are troublesome and inefficient, and it is extremely difficult to eliminate other fructose polymers; thus, it is impossible to avoid great disadvantages that the purity of DFA III is low with a peculiar residual smell since these polymers are remaining unremoved, and that smell remained.

In a method of using an active carbon column, other fructose polymers than DFA III, and impurities such as pigments are non-selectively adsorbed once on active carbon, from which a series of fractions are eluted with ethanol, and the fractions rich in DFA III are collected to recover DFA III. Contrary, the process for purification of the invention is quite different in its law since a small amount of powdered active carbon is added to an enzyme reaction solution to make impurities adsorb (most of DFA III is remaining unremoved in the solution) and then removed; further, since the way of operation, efficiency of operation and the degree of purification are quite different and the kind, particle size and amount of active carbon to be used are also different, the method of the prior art is quite different from that of the present invention, indicating that there is no relationship with the patentability of the invention. Thus, both methods are quite different from each other.

In this connection, Example 4 of the Patent Document 4 (ion-exchange method) describes a step which comprises filtering a supernatant of Jerusalem artichoke through Celite and treating the filtrate with active carbon; this step, however, is carried out as a pre-treatment step or a simple starting step for partial purification in order to smoothly conduct the subsequent treatment with an ion-exchange resin with no trouble since the supernatant of Jerusalem artichoke contains much impurities. Thus, such a step is quite different from the treatment with active carbon employed in the invention in its technological significance. In the above reference, there is no definition about the particle size and amount of the active carbon to be used, and further no description on a specified DFA III solution as an object to be treated (a purified DFA III solution in the invention) containing a specified concentration of DFA III of specified purity (it is apparent that the supernatant of Jerusalem artichoke is different from the specified DFA III solution used as a purified solution of DFA III in the invention). In addition, though a step of crystallization is carried out after purification with active carbon in the invention, treatment with an ion-exchange resin which is quite different therefrom is made but no crystallization is made in the cited method. Further, no deodorization is made. Thus, this method has no relation to the process of the invention.

In order to produce highly pure crystals of DFA III in the invention which is quite different from the prior art, it is appropriate to use as a starting crude material for crystallization a crude solution of DFA III which contains DFA III of 60% or more purity, preferably 70% or more, at a concentration of R-Bx 60 or more, preferably 70 or more. Using this peculiar crude solution of DFA III, pure crystals of DFA III, 95% or more in purity or 99% or more, can be produced effectively in a recovery rate of 35% or more (for inulin) on a large scale. As for the crude solution of DFA III, at least one of DFA III containing crude solution, DFA III fractions obtained by chromatography, and crystal syrup or crude crystal syrup may be used.

Such a DFA III containing solution can be obtained by treating inulin with an enzyme, wherein the polymerization degree of fructose is 10 or more, preferably 10 to 100, more preferably 10 to 60. When the solution contains less pure DFA III, it may be applied to chromatography (hereinafter sometimes referred to as chromato) to recover the above-mentioned specific fraction of DFA III. If required, the components may be adjusted by a conventional way such as concentration, centrifugation, filtration, and others, to prepare a DFA III solution comprising the above mentioned components.

An enzyme which catalyses transfer of a fructose unit to synthesize oligo-saccharides is "fructosyltransferase" in the broad sense. Fructosyltransferase can roughly be classified into two types. (1) Enzyme acting on the fructose unit (including disaccharides such as sucrose) as substrate and hydrolyzing/transferring it to synthesize oligosaccharides (in some cases, polysaccharides synthesized). (2) Enzyme acting on fructan as substrate such as inulin or levan and hydrolyzing/transferring it to synthesize oligosaccharides. Among them, the chemical name of fructosyltransferase used in production of DFA III from inulin by the present inventors is inulin fructotransferase, which belongs to the type (2). As for microorganisms producing inulin fructotransferase (hereinafter abbreviated to as IFT), bacteria belonging to *Arthrobacter, Kluyveromyces, Streptomyces* and *Enterobacter*, yeast, and *Actinomyces* have been reported and can optionally be used. These microorganisms may be cultured and properly be used in a form of purified enzyme, crude enzyme, enzyme-containing material, microorganism culture, and the like.

The followings are non-limited examples: *Arthrobacter* sp.; *Arthrobacter ureafaciens* IFO 12140; *Arthrobacter globiformis* IFO 12137; *Arthrobacter pascens* IFO 12139; *Bacillus* sp.; *Kluyveromyces marxianus* var. *marxianus*; *Streptomyces* sp.; and *Enterobacter* sp.

When an enzyme derived from these microorganisms is used, it may be used as an isolated and purified enzyme, as well as roughly purified enzyme, microorganism culture, processed material of the same (culture supernatant, isolated cells, crushed cells). DFA III crystals, when used in food, it is appropriate to use a fructosyltransferase as an enzyme, particularly IFT. In particular, in addition to the above enzymes derived from microorganisms, an enzyme derived from *Arthrobacter* sp. AHU 1753 strain (deposited as the accession no. FERM BP-8296 at International Patent Organism Depositary) may preferably be employed since it has a much better productivity for IFT.

It is most preferred that DFA III might be produced as a single product from inulin by degradation with an enzyme, but practically other fructose polymers than DFA III are produced. This is a cause of decrease of the purity of an enzymolytic solution. Therefore, it is necessary to choose a starting material which yields least contamination of impurities other than inulin for crystallization of DFA III or an enzyme which yields no fructose polymers but DFA III. If such a DFA III containing solution rich in DFA III is obtained, it would be possible to use it per se as a crude solution of DFA III for defecation and filtration, and crystallization in the invention.

The invention will be explained in detail with reference to a flow chart of production as shown in FIG. 1 as an example of the flow of production of crystalline DFA III.

Inulin is treated with inulin hydrolase, which is then deactivated to give a DFA III solution (enzyme reaction solution). In this operation, it is appropriate to use a starting inulin of which the fructose polymerization degree is 10 or more, preferably 10 to 60, in order to efficiently produce highly pure DFA III crystals. As for an enzyme, the above-mentioned one may optionally be used (preferably, for example, IFT derived from *Arthrobacter* sp. AHU1753 strain (FERM BP-8296)), and enzyme treatment and deactivation may be carried out in a conventional way. Thus, a DFA III solution in which R-Bx (Refractometric Brix) is 10 or more, preferably 15 or more, more preferably 20 or more, and even more preferably 20 to 30, and in which the purity of DFA III is 60% or more, preferably 65% or more, more preferably 70% or more, and even more preferably 70 to 85%, can be obtained. According to a chemical synthesis, a DFA III solution can also be prepared as well. As described above, it is appropriate to use a starting material inulin of which the fructose polymerization degree is 10 or more, though it is also possible to use inulin of which the fructose polymerization degree is, for example, approximately 5, because it can satisfactorily be treated in the invention even though syrup as by-product is increased and the frequency of circulating treatment is increased.

At least one of the DFA III containing solution prepared as above, a DFA III fraction(s) having the same properties obtained by chromatographic treatment, and crystal syrup or crude crystal syrup, is then applied to defecation and filtration. Defecation and filtration means treatment of the DFA III crude solution with active carbon and subsequent solid-liquid separation. Treatment with active carbon may be carried out by adding a small amount of powdered active carbon to a DFA III crude solution, and if required heating and/or stirring the mixture to make impurities other than DFA III adsorb on active carbon.

As powdered active carbon, that of 15-50 microns in average particle size, preferably 25-45 microns, more preferably about 35 microns; and 200 microns or less in maximum particle size, preferably 170 microns or less, more preferably 150 microns or less, for example, 147 microns or less, may be used. The amount to be added to the solid content is fixed at 5% or less, preferably 0.1-3%, and more preferably 0.5-1.5%, which may optionally be adjusted according to the composition of DFA III crude solution.

Solid-liquid separation may optionally be achieved by at least one operation including filtration with a filter aid such as Hi-Flo Supercell (Wako Pure Chemical Ind.) or diatomaceous earth filter (for example, filtration with a ceramic filter; Japan Pole KK.: PR-12 type available), filtration with a membrane filter (MF), continuous centrifugation, molecular sieve method, reverse osmotic membrane method, ultra-filter (UF) membrane in some cases, and the like. Solid-liquid separation is carried out under atmospheric, increased or reduced pressure.

In the above operation, the solid-liquid separation can be carried out directly without using any filter aid such as diatomaceous earth when the separation is conducted, for example, by filtration with an ultra-filter membrane (UF membrane) or filtration with a membrane filter (MF) or continuous centrifugation. As MF membrane, for example, a ceramic membrane (e.g., trade name: Dahlia; Tsukishima Machine Co.) may be used. According to continuous centrifugation (5,000-25,000 rpm, preferably 8,000-15,000 rpm; 6,500-10,000 G, preferably 7,500-9,500 G; e.g., 10,000 rpm, 8,200 G), crystals of DFA III (crystal size 250-500 µm) can be separated from fine crystals (crystals other than DFA III, mainly tetra- and penta-saccharides; crystal size 100 µm or less); thus, this can be applied to solid-liquid separation of crude crystal syrup or crystal syrup.

The filtrate obtained by solid-liquid separation is then concentrated. The concentration may be achieved in a conventional way, for example, using an evaporator for concentration. The resulting condensate which is a mother liquor of crude crystals is converted into crude crystals by evaporation for crystallization or by crystallization under cooling. Roughly crystallized mother liquor is divided into crude crystals and crude crystal syrup. In this separation, centrifugation may be applied.

The crude crystal syrup and the crystal syrup separated from the crystallized mother liquor are applied to solid-liquid separation by for example continuous centrifugation (e.g., Alfa Laval Co.). The syrup contains non-crystallized oligo-saccharides other than DFA III, of which the fructose polymerization degree is diverse. It has been found that the higher degree of fructose polymerization makes crystallization easy and yields crystals smaller in particle size. Utilizing this property, DFA III can be separated from other oligo-saccharides. Thus, oligo-saccharides other than DFA III can be eliminated to prevent circulatory accumulation of oligo-saccharides other than DFA III and suppress decrease of the purity of the starting material for crystallization of DFA III. When the oligo-saccharides other than DFA III is accumulated by circulation, the purity of crude crystal mother liquor (condensate) is decreased, and it becomes difficult to retain the purity at which efficient (industrial) crystallization can be achieved (60% or more purity in crude crystals). Particularly, syrup may be removed outside the production system in order to prevent decrease of the purity of the crude crystal mother liquor (condensate), but it should be avoided because it is accompanied by loss of DFA III.

The filtrate obtained by defecation and filtration of a DFA III containing solution (crude solution) is concentrated in a conventional way. For example, the filtrate is concentrated in a calandria evaporator, which is used in production of sugars, to give a condensate. The condensate may be condensed up to a concentration of R-Bx 60 to 85, preferably 65 to 80, for example, about 77.

The condensate is crudly crystallized optionally by a conventional crystallization way such as evaporating crystallization using a boiling pan or cooling crystallization using a cooler. The boiling pan for evaporating crystallization means, for example, those used in production of sugars. As a crystallizer under cooling, the same type as those used in production of sugars, i.e., a horizontal type or vertical type crystallizer, may be used. Thus, a DFA III containing solution which is supplied into the boiling pan or cooler is called the crude crystal mother liquor (condensate). During rough crystallization of DFA III, it is appropriate to handle the crystals so that they do not adhere to the inner wall of the boiling pan or cooler. For example, a stirrer attached to the boiling pan or cooler is effective in an increase of crystallinity. As a centrifugal machine, those used in production of sugars may be used. Crude crystals of DFA III may be dried at a temperature of 50 to 100° C. under atmospheric pressure. Drying under reduced pressure is also acceptable.

A mother liquor (condensate) in which DFA III crystalized during crude crystallization is subjected to solid-liquid separation to give crude crystals (the purity of DFA III reaches 95-98%) and crude crystal syrup. The solid-liquid separation may be carried out in a manner as mentioned above; for example, both are separated, as described above, by means of a centrifugal machine (at 500-6,000 rpm, preferably 1,000-5,000 rpm; for example, 2,000-4,000 rpm, 500 G-3,000 G, preferably 800-2,000 G, for example, 1,200 G); the crude crystal syrup, after or without solid-liquid separation, is, if required, returned to the purification step, in which the crude crystals are dissolved again in water or hot water to give a redissolved solution, which is used as a DFA III containing purified solution for use in a crystal mother liquor used for crystallization of the final product.

The redissolved solution (a DFA III containing purified solution: R-Bx is 10-60, preferably 20-55, more preferably 40-50; DFA III purity is 90% or more, preferably 90-98%, for example, it reaches about 95-98%) may be used in production of the product of DFA III crystals (purity: 98-99% or more; highly purified crystals with no color and no smell) in the same manner as in the above-mentioned crude crystals, that is, through defecation and filtration, concentration of the filtrate, crystallization of the condensate (a crystal mother liquor for the final product) for a product, separation of the product crystals and crystal syrup, and drying and packaging of the product crystals (DFA III purity is 98-99% or more, highly pure DFA III crystals having no color and smell). The syrup (crystal syrup, crude crystal syrup), if required, after or without solid-liquid separation, may be returned to at least one of the any purification steps from the DFA III containing solution to the product crystals of DFA III (the flow as shown in FIG. 1).

Figure 2:
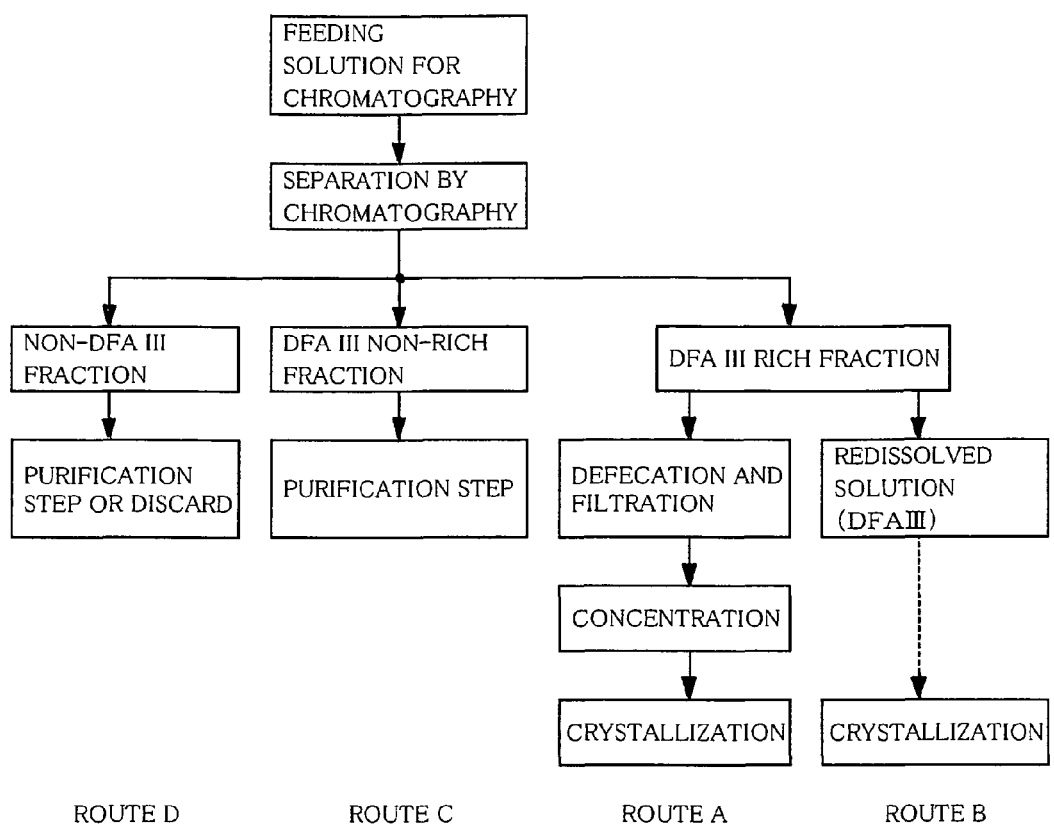
FIG. 2 shows an example of a flow chart illustrating purification by chromatography.

In the invention, it is also possible to produce the DFA III crystals utilizing chromatographic separation. That is, a variety of the products produced in the total purification steps (FIG. 1) in crystallization of DFA III may be used as the feeding solutions in chromatography (R-Bx: 40-75) and they may be chromatographed and purified, followed by crystallization. FIG. 2 shows an example of the purification flow by chromatography.

The feeding solutions for chromatography (R-Bx: 40-75) are chromatographed to separate a DFA III fraction. The fraction rich in DFA III which has the same degree of purification as in the above-mentioned redissolved solution (DFA III solution) is subjected as a DFA III containing purified solution to defecation and filtration, concentration and crystallization, to yield the final product of crystals (Route A). Alternatively, the DFA III-rich fraction is added to the above redissolved solution (DFA III solution) and the resulting DFA III containing purified solution may be crystallized (Route B). A fraction non-rich in DFA III, of which the DFA III content is low differently from the fraction rich in DFA III, may be returned to an optional step of the production flow (the total steps through the DFA III containing solution to the product of DFA III as shown in FIG. 1) (Route C). A non-DFA III fraction which contains a least amount of DFA III may be returned to the purification steps or if necessary discarded (Route D).

When a DFA III containing solution (40% or more purity) is chromatographed, the resulting DFA III fraction has 70-98% purity; in order to obtain a DFA III rich fraction having 85% or more purity, preferably 90-95%, if required 95-98%, the purification may be made according to Route A through defecation and filtration, concentration and crystallization for the product. Thus, for example, a mother liquor (condensate) for crude crystals, not through a step of crude crystallization, is chromatographed to separate a DFA III fraction (DFA III rich fraction), which as a DFA III containing prified solution is treated with active carbon and the resulting condensate is used as a mother liquor for the product crystals and treated in the same manner as mentioned above to yield odorless and highly purified product crystals of DFA III. Of course, this fraction may be added to the redissolved solution and treated as a solution for purification of DFA III, for example, according to Route B. The fraction non-rich in DFA III separated as mentioned above may be returned to the purification steps (the total purification steps involving from a DFA III containing solution to a DFA III product) according to Route C, for example, an optional step as shown in FIG. 1; thus, the purification steps as a whole can thoroughly be made more efficient by cycling the present flow without producing any waste and loss.

When inulin less contaminated with impurities is used, for example, when inulin of which the fructose polymerization degree is 10 or more, preferably 10-60, and the polysaccharide content is 80% or more, preferably 100% inulin is used as a starting material, treatment with a purified enzyme as fructotransferase and subsequent chromatography of the resulting DFA III solution afford a fraction rich in DFA III, which can be directly concentrated and crystallized without defecation and filtration with active carbon. The DFA III crystals obtained have no smell and color and show extremely high purity. This indicates that the use of highly pure inulin and/or purified fructosyltransferase produce odorless and highly pure crystals of DFA III very efficiently through only one round of separation, concentration and crystallization without defecation and filtration.

Chromatographic separation can be accomplished by using a separation apparatus of static bed system (one-pass system), continuous system (simulated moving bed system), or semi-continuous system (a combination of static bed system and continuous system). The ion-exchange resin to be packed into the apparatus includes strongly acidic ion exchange resins of Na type, K type or Ca type for use in chromatography. As the resin, a styrene divinylbenzene resin homogeneous in particle size may be used. Diverse types of commercially available chromatographic resins supplied by manufacturers of the chromatographic resin can be employed as far as they are applicable to sugar solutions. When the purity of DFA III in a crystal mother liquor is low, chromatography can be applied in order to raise the purity.

In the invention, a DFA III containing solution (crude crystal mother liquor) of DFA III of which the purity is less than 70% can be crystallized on an industrial scale.

In the invention, in order to raise the degree of purification of a DFA III containing solution of which the purity is less than 70%, the DFA III containing solution may be applied to at least one operation, i.e., treatment with yeast, defecation and filtration or chromatography; by this operation, the purity of DFA III contained in the solution can greatly be raised.

The present invention relates to a process for purifying a DFA III containing solution by at least one operation selected from treatment with yeast, defecation and filtration and chromatography. Utilizing the process of the invention, highly pure DFA III crystals can be produced efficiently on an industrial scale. The DFA III containing solution means all of liquid materials containing DFA III and satisfying the conditions as described below. Such liquid materials include all kinds of liquids containing DFA III, that is, reaction mixtures in which DFA III has been generated from a fructose polymer, for example, inulin or an inulin solution, on action of a fructosyltransferase, as well as a variety of solutions of biologically synthesized DFA III, solutions of chemically synthesized DFA III, solutions containing DFA III purified at diverse levels produced in the purification steps of the invention, and liquids in which commercially available DFA III is dissolved.

For example, when DFA III is produced from inulin (and/or an inulin solution) using an enzyme, inulin is used as an extract extracted mainly from Jerusalem artichoke (or chicory, burdock, etc.), in which inulin composed of one glucose and a multiple of fructose attached to the glucose, and which is commercially available at diverse levels of polymerization degree and purity. When it is degraded with an enzyme, the resulting reaction mixture contains unavoidably impurities, such as fructose polymers other than DFA III, enzyme, microorganism used as an enzyme source, other cultures, pigments, smell, etc. Thus, it was not possible in the prior art to obtain purified DFA III, i.e., pure DFA crystals or materials containing it, on an industrial scale at low cost.

In crystallizing out DFA III from a DFA III solution, the lower limit of the industrially and economically acceptable purity of crystallizable DFA III is 60% (more than 70% being better). In other words, it is impossible to crystallize out DFA III industrially and economically from a solution of DFA III of which the purity is 60-70% or lower, and in the prior art, accordingly, a DFA III containing solution of which the purity is 70% or lower could not be employed because of unprofitable industrial crystallization (much less in a case of a DFA III solution of 60% or less purity).

In view of the above-mentioned state, a process for highly purifying DFA III from a DFA III containing solution which has not long been used industrially because of its low purity has been developed in the invention; for example, in order to efficiently obtain DFA III highly purified so that pure DFA III crystals can be obtained from it, investigation has been made from various views, and as a result a novel process which comprises subjecting a DFA III solution to at least one operation, i.e., chromatography (hereinafter sometimes referred to as chromato-treatment), defecation and filtration, and treatment with yeast has been developed.

As for the DFA III solution, as described above, solutions of biologically synthesized DFA III, solutions of chemically synthesized DFA III, solutions in which commercially available DFA III is dissolved, and solutions containing DFA III of which the purity is low, can be used.

In the invention, it is possible to use a solution containing highly pure DFA III as well as a solution of less pure DFA III as a DFA III solution as described above, and at least one operation, i.e., treatment with yeast, defecation and filtration or chromato-treatment makes it possible first time to use a less pure DFA III solution (purity 70% or less, possibly 60% or less) as starting material, which has not long been used because of economical or industrial reasons, and to purify DFA III efficiently.

First, the treatment with yeast may be carried out by bringing a DFA III solution contact with yeast, if required with stirring in an incubation condition, or incubated under aeration. As for yeast, baker's yeast, Japanese sake yeast, beer yeast, wine yeast, and other yeast may optionally be used. It is also possible to use dry yeast, compressed yeast and other various commercially available types of yeast, satisfactorily. Since yeast acts on disaccharides or monosaccharide to degrade or incorporate in the microorganism, the treatment with yeast is effective in removing disaccharides and/or monosaccharide outside the system.

The defecation and filtration is intended for defecation by treatment of a DFA III solution with active carbon and solid-liquid separation. The operation for the solid-liquid separation includes centrifugal separation, filtration, filtration with a filter aid such as diatomaceous earth, a method of using membrane filters, a method of using ceramic membranes, a method of using a ultra-filer membrane, and other methods for solid-liquid separation.

The chromato-treatment may optionally be carried out with an ion-exchange resin for chromatography by means of a static bed, continuous bed (simulated moving bed), or semi-continuous system, to separate disaccharides from other saccharides. Thus, DFA III, a disaccharide, can be separated from other saccharides efficiently by chromatography.

Thus, when the disaccharide contained there is DFA III alone, chromatography is highly effective in purification of DFA III. Separation of DFA III from other disaccharides, however, is very difficult because they all are disaccharides. Accordingly, a DFA III containing solution prepared from inulin by treatment with an inulin hydrolytic enzyme, for example, contains a disaccharide sucrose in addition to another disaccharide DFA III; in such a case, it becomes very difficult to separate DFA III from sucrose (another disaccharide) by chromato-treatment. In such a case, DFA III can effectively be purified in combination with another type of operation. For example, a DFA III containing solution is treated with yeast as pre-treatment to remove other disaccharides than DFA III outside the system, and then chromatographed.

Thus, in the invention, the optimum treatment selected from yeast treatment, solid-liquid separation and chromatography depending on the DFA III solution may be made. If required, these operations may optionally be used together or combined, or alternatively each operation or plural operations may further be repeated. Thus, a less pure DFA III solution which could not be used industrially in the prior art can effectively be purified for the first time.

For example, in a solution of biologically synthesized DFA III, fructose polymers can be used as a starting material, on which fructosyltransferase is allowed to act to yield DFA III.

In such a case, as the fructose polymer used as a starting material, naturally occurring polymers such as inulin, as well as biologically and/or chemically synthesized polymers may be used, though the degree of polymerization of fructose is 2 or more, preferably 10 or more, and more preferably 10-60. The content of polysaccharide in the polymer is preferably 70% or more, and more preferably 100%. In the invention, however, a less pure DFA III solution can also be purified efficiently; thus, a low-grade fructose polymer can optionally be used in the same way as the high-grade polymer.

In the invention, the fructose polymer may be a homo-polymer which is composed of fructose only or a hetero-polymer which may contain any other type of saccharide; for example, inulin is a kind of hetero-polymer in which one molecule of glucose is attached to a fructose polymer. In addition, the fructose polymer includes materials containing a fructose polymer.

Among these fructose polymers, a naturally occurring product inulin is used advantageously, though a biologically or chemically synthesized polymer may be used. For example, the following biosynthetic polymers may be used.

For example, inulin can be synthesized biologically by making a fructose synthetase (e.g., inulin synthetase) act on sucrose. As an inulin synthetase, sucrose:sucrose 1-fructosyltransferase (SST) and β-(2-1)fructan: β-(2-1)fructan 1-fructosyltransferase (FFT) may be used. An enzyme produced by a microorganism such as Aspergillus sydowy IFO4284, IFO7531, or Streptococcus mutans produces inulin analogues. These inulin analogues are also fructose polymers and/or fructose polymer-containing materials, and can be used as starting materials for DFA III solutions in the invention.

When glucose is produced as a by-product in production of fructose polymers such as in biosynthesis, it is also possible to convert glucose into fructose by an enzyme such as glucose isomerase which can convert glucose into fructose, or to convert glucose into a different material by an enzyme such as glucose oxidase which can convert glucose into gluconic acid, in order to reduce the amount of glucose and increase the yield of inulin (or inulin analogues). It is also possible to add yeast to a DFA III solution and incubate the mixture under aeration and agitation for yeast treatment in order to make impurities other than DFA III consumed by yeast and increase the purity of the DFA III solution before chromatography.

The following example will illustrate the treatment of a fructose polymer as a DFA III containing solution using fructosyltransferase, wherein the fructose polymer is inulin.

An enzyme which catalyses to transfer a fructose unit to yield an oligosaccharide such as DFA III is "fructosyltransferase" in the broad sense. Fructosyltransferase can roughly be classified into two types. (1) Enzyme acting on the fructose unit (including disaccharides such as sucrose) as substrate and hydrolyzing/transferring it to synthesize oligosaccharides (in some cases, polysaccharides synthesized). (2) Enzyme acting on fructan as substrate such as inulin or levan and hydrolyzing/transferring it to synthesize oligosaccharides. Among them, the chemical name of fructosyltransferase used in production of DFA III from inulin by the present inventors is inulin fructotransferase, which belongs to the type (2). As for microorganisms producing inulin fructotransferase (hereinafter abbreviated to IFT), bacteria belonging to *Arthrobacter, Kluyveromyces, Streptomyces* and *Enterobacter*, yeast, and *Actinomyces* have been reported and can optionally be used. These microorganisms may be cultured and properly be used in a form of purified enzyme, crude enzyme, enzyme-containing material, microorganism culture, and the like.

The followings are non-limited examples: *Arthrobacter* sp.; *Arthrobacter ureafaciens* IFO 12140; *Arthrobacter globiformis* IFO 12137; *Arthrobacter pascens* IFO 12139; *Bacillus* sp.; *Kluyveromyces marxianus* var. *marxianus; Streptomyces* sp.; and *Enterobacter* sp.

When an enzyme derived from these microorganisms is used, it may be used as an isolated and purified enzyme, as well as roughly purified enzyme, microorganism culture, processed material of the same (culture supernatant, isolated cells, crushed cells, etc.). DFA III crystals, when used in food, it is appropriate to use a fructosyltransferase as an enzyme, particularly IFT. In particular, in addition to the above enzymes derived from microorganisms, an enzyme derived from *Arthrobacter* sp. AHU 1753 strain (deposited as the accession No. FERM BP-8296 at International Patent Organism Depositary) may preferably be employed since it has much better productivity for IFT.

It is most preferred that DFA III might be produced as a single product from inulin by degradation with an enzyme, but practically other fructose polymers than DFA III are produced. This is a cause of decrease of the purity of an enzymolytic solution. Therefore, chromatography is conducted, but if required it is necessary to choose a starting material which yields least contamination of impurities other than inulin for crystallization of DFA III or an enzyme which yields no fructose polymers but DFA III. If such a pure solution of DFA III is obtained, it would be possible to use it per se as a crude solution of DFA III for a step of defecation and filtration and crystallization in the invention.

The purity of DFA III in a DFA III solution prepared by degradation of inulin with an inulin hydrolytic enzyme will be shown as an example for the products of the firms A to D as mentioned below.

The product of the firm A: 75%; the product of the firm B: 59%; the product of the firm C: 52%; the product of the firm D: 78%.

Additionally, as another example, the purity of DFA III in a syrup prepared for crystallization by degradation of inulin of the firm D with an inulin hydrolytic enzyme is as follows:

Crude crystal syrup 53%; syrup for product crystal 95%

A variety of DFA III solutions prepared not only by treatment with an enzyme such as IFT as described above but also by other methods can be subjected to at least one operation, i.e., chromatography (hereinafter sometimes referred to as chromato-treatment), treatment with yeast or defecation and filtration to eliminate impurities to yield DFA III of the diverse degrees of purification.

In such a case, a highly purified DFA III solution affords a highly pure DFA III (the purity as high as it may be used immediately in the step of crystallization yielding highly pure crystals). On the other hand, a less purified DFA III solution affords a less pure DFA III, which can be further purified by repetition of the above operation, e.g., chromato-treatment. According to the invention, it is possible to obtain DFA III of the desired purity optionally from a DFA III solution of the diverse degrees of purification.

A DFA III containing solution can highly be purified by chromatography, by which impurities are eliminated. A less purified fraction may also be purified by repeating once more or more times chromatography or other operations for purification.

Though a DFA III solution may be applied as such to chromatography, treatment such as concentration for increasing the concentration of the solution improves the efficiency. The treatment for concentration may be carried out for example in an evaporator (e.g., 50-80° C., 140 mmHg or lower). Other type of treatment for concentration may also be employed optionally.

A preferred example of the invention is exemplified by the following process for purification. First, inulin which is commercially available as a raw material or biologically synthesized from sucrose is allowed to contact with IFT (enzyme treatment), and the resulting DFA III solution is chromatographed to eliminate contaminated impurities for purification. During this operation, if required, other operations for purification, e.g. treatment with yeast, may optionally be conducted.

According to the invention, even a less pure DFA III solution can be purified by at least one operation, i.e., chromatography, treatment with yeast or defecation and filtration, to yield a pure DFA III solution efficiently on an industrial scale.

The resulting pure DFA III solution can widely be applied to a variety of uses. According to the invention, a DFA III containing solution can be purified at a level as high as it can be crystallized immediately. Thus, it is possible to produce highly pure crystals of DFA III of which purity is 95 w/w % or more, crushed crystals, or granular crystals, which can widely be utilized in various uses such as drugs or supplement.

The invention also relates to an efficient process for large scale production of fructosyltransferase such as inulin fructotransferase (sometimes abbreviated to as IFT).

In the invention, it has been found for the first time that the production of the enzyme is remarkably increased in the amount by addition of inulin without decreasing the activity. Thus, it is possible to produce IFT on a large scale even in a tank as large as 200 liters or more volume.

The enzyme in question can be produced by incubating a microorganism producing the same (including those which exogenously secret the enzyme and/or those which endogenously accumulate the enzyme) and recovering it from the culture, wherein the incubation has to be conducted in a medium to which inulin has been added. The amount of inulin to be added is 0.1-10%, preferably 0.5-5%; for example, a culture medium to which inulin has been added at about 1% may be used.

In addition, it is appropriate to add a trace amount of yeast extract to the culture medium as a nutrition source at a rate of 0.02-2.0%, preferably 0.1-1.5%; for example, a culture medium to which an yeast extract has been added at about 0.5% may be used.

In carrying out the invention, a microorganism producing said enzyme may be incubated in a culture medium to which inulin has been added as mentioned above (preferably, a medium to which an yeast extract has been added). In this incubation, there is no particular limitation in the composition of the medium and the condition of incubation, and the incubation may be carried out depending on the microorganism to be used, under aeration of 0.5 vvm or more, preferably 1-2 vvm.

According to the process of incubation of the invention, the enzyme in question can be produced on a mass-production scale. In the prior art, the amount of the enzyme produced was from 1 unit (enzymatic unit)/ml to at most several ten unit/ml (culture medium). In this invention, contrarily, it becomes possible to produce the enzyme at a extremely high activity (several hundred unit (enzymatic unit)/ml (culture medium) or more).

Moreover, this remarkable effect is recognized not only in an experiment at a laboratory level or a small scale production but also in a case using a huge fermentation apparatus for microorganisms, for example, a huge fermentation tank of 50 liters or more, or of 100 liters or more. It has been confirmed that a jar fermentor of 200 liter volume can be used, and additionally, for example, a fermentation tank of 300-500 liter volume can also be used.

Thus, the present invention makes it possible for the first time to produce a large quantity of enzymes without decreasing the enzymatic activity at all. The characteristics are shown as follows.

(Relating to an Incubation Apparatus)

(1) A large-scale fermentation apparatus was introduced.

Since the preparation of fructosyltransferase has been succeeded at a laboratory level, this item for development is readily conceivable. Expansion of the fermentation apparatus, however, results in marked decrease of the active value of an inducible enzyme compared with that at the laboratory level in many cases. It is a new great discovery that the active value in fact ascends by use of a 200-liter or larger tank.

(Relating to a Method for Incubation)

(2) The optimum amount of an enzyme inducible material inulin was determined in accordance with a large-scale fermentation apparatus.

(3) An yeast extract was found as a factor for the amount of production and increase of the stability of the enzyme, and the optimum amount to be added was determined in accordance with a large-scale fermentation apparatus.

(4) The amount of air to be supplied during the fermentation was found as a factor for increase of the amount of production of enzyme, and its optimum amount was determined in accordance with a large-scale fermentation apparatus.

As the microorganisms to be used, those belonging to *Arthrobacter, Kluyveromyces, Streptomyces, Enterobacter, Bacillus* and *Microbacterium*, as well as a variety of bacteria, yeast, mold, actinomycetes, and the like, may optionally be used.

The followings are non-limited examples of the microorganisms which can be used in the invention: *Arthrobacter ureafaciens*, the same (IFO 12140), the same (ATCC 21124), *A. pascens* (IFO 12139), the same T13-2, *A. globiformis* (IFO 12137), the same C11-1, *A. nictinovorans* GS-9, *A. ilicis* OKU 17B, *Arthrobacter* sp., the same H65-7, the same AHU 1753 (FERM BP-8296), the same MCI-2493; *Kluyveromyces marxianus* (ATCC 12424), the same CBS 6556, *K. marxianus* var. *marxianus*, the same (IFO 1735); *Streptomyces fumigatus, S. rochei*, the same E87, *Streptomyces* sp., the same MCI-2524; *Pseudomonas fluorescens*, the same No. 949; *Bacillus circulans*, the same OKUMZ. 31B, the same MCI-2554, *Bacillus* sp., the same Snu-7; *Aureobacterium* sp., the same MCI-2494; *Microbacterium* sp., the same AL-210; *Enterobacter* sp., the same S45; *Aspergillus fumigatus; Penicillium purpurogenum*.

In producing the enzyme, for example, a microorganism producing it as described above is used; it may be incubated in a conventional manner except for a certain condition as defined above, and the resulting enzyme may be extracted and purified according to a convention manner in production of enzymes. For example, the resulting culture is centrifuged to remove the cells, the filtrate subjected to salting-out with addition of ammonium sulfate (65% saturated), and the precipitate collected by centrifugation, dispersed in a small amount of water, and dialyzing to yield a crude enzyme solution. This solution, if required, may further be purified in a conventional manner, for example, one or two or more known purification methods such as chromatography to yield a pure enzyme.

In this connection, when the microorganism producing the enzyme in question is not an exogenous secretion type but an endogenous accumulation type, the cells are separated from the culture, and destroyed by a conventional cell crushing treatment, for example, ultra-sonication, from which the enzyme may be isolated and purified.

In addition, the invention makes it possible to produce the enzyme not only on a small scale but also on a large scale, for example, in a huge fermentation tank of 200 liters or more, or of 500 liters or more, with no adverse effect and without decreasing the enzymatic unit in the above-defined culture condition. Thus, the invention allows the large-scale production of highly active enzyme and particularly provides an industrially superior effect.

The enzyme used in the invention includes an isolated and purified enzyme, as well as roughly purified enzyme, microorganism culture, processed material of the same (culture supernatant, isolated cells, crushed cells). DFA III crystals, when used in food, it is appropriate to use a fructosyltransferase as an enzyme, particularly IFT. In particular, in addition to the above enzymes derived from microorganisms, an enzyme derived from *Arthrobacter* sp. AHU 1753 strain (deposited as the accession No. FERM BP-8296 at International Patent Organism Depositary) may preferably be employed since it has a much better productivity for IFT.

The enzyme thus produced on a large scale per se can be utilized as a reagent for some research use and also applied to a variety of purposes, one of which is the action of the enzyme on inulin to synthesize various oligosaccharides. For example, a fructosyltransferase is allowed to act on inulin of which the fructose polymerization degree is 10 or more, preferably 10-60, to produce a DFA III containing solution. In this operation, as an inulin fructotransferase (depolymerizing), at least one of purified enzyme, roughly purified enzyme, enzyme-containing material, cells, cell culture, and its processed material derived from *Arthrobacter* sp. AHU 1753 strain (FERM BP-8296) may be used.

Thus, since it is now possible to produce a DFA III solution efficiently at low costs, it can be applied to obtain highly pure crystals of DFA III with no smell. In this purification, for example, powdered active carbon is added to the DFA III solution at a rate of 5% or less to the solid content, and after defecation and solid-liquid separation, the separated liquid portion is concentrated and immediately crystallized out; if required, this operation may be repeated or combined with chromatography for further purification.

The invention will be explained in more detail by the following examples.

EXAMPLE 1

Polymerization Degree of Fructose in Inulin

Molecular Weight Distribution

Figure 3:
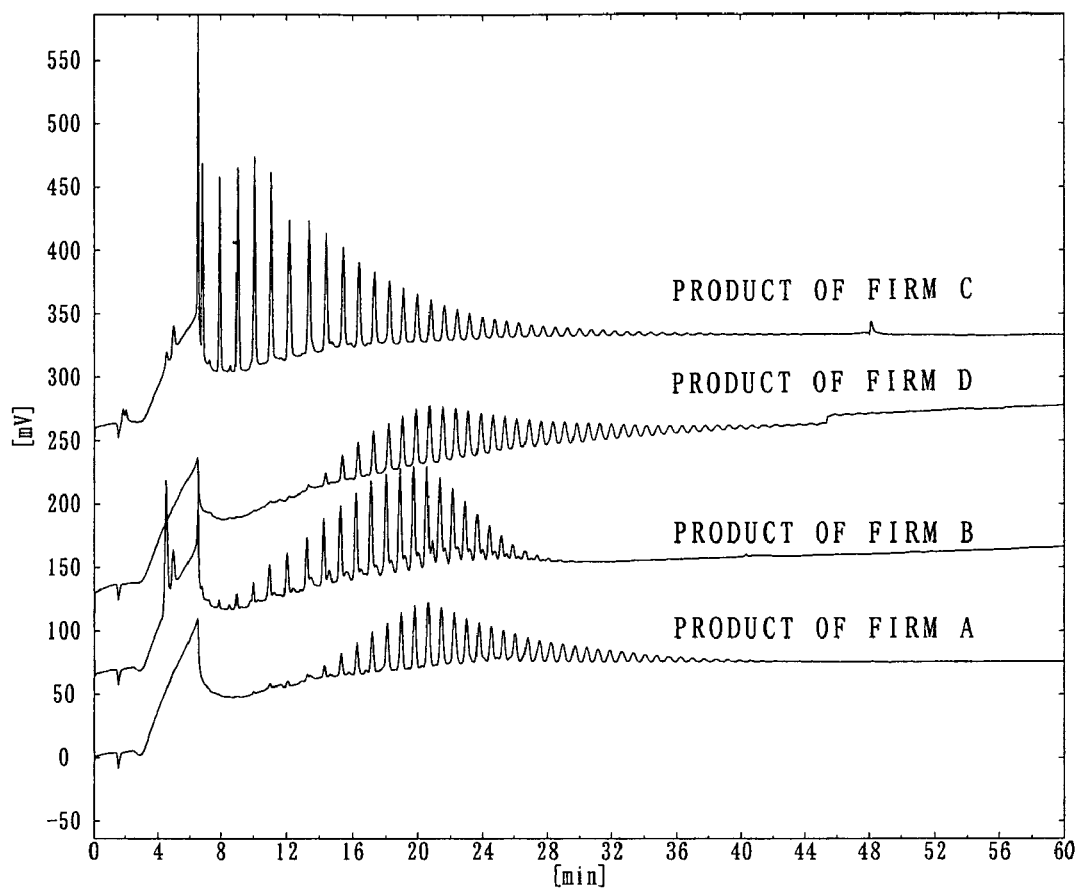
FIG. 3 shows a liquid chromatogram of a variety of commercially available inulins.

Commercially available inulin was purchased and its fructose polymerization degree was investigated. A chromatogram as shown in FIG. 3 was made in the following condition using a liquid chromatography analyzer.
1) Samples to be Analyzed of Inulin
  a) Product of Firm A
  b) Product of Firm B
  c) Product of Firm C
  d) Product of Firm D
The indication of the above samples as shown in Catalogues is shown in the following table 1.

TABLE 1

|  | Sample | | | |
| --- | --- | --- | --- | --- |
|  | a | b | c | d |
| Chemical structure | GFn | GFn | GFn | GFn |
| Polymerization range |  |  | 2-60 | 10-60 |
| Mean degree of Polymerization |  | 18 | 10-12 | 20-25 |
| Production |  | Enzyme synthesis from sugar | Extract from chicory | Separation of inulin |
| Polysaccharide content |  |  | ca. 70% | 100% |

GFn:
G: Glucose
F: Fructose
n: number of polymerization

2) Analysis Condition
  Column: Dionex, CarboPac PA1, 4×250 mm I.D.
  Guard column: Dionex, CarboPac PA1 Guard
  Column temperature: room temperature
  Eluent: Gradient

|  | 0 min. Rate (%) | 100 min. Rate (%) |
| --- | --- | --- |
| 1N-NaOH | 15 | 15 |
| 1M-NaOAc (1M sodium acetate) | 0 | 45 |
| Water | 85 | 40 |
| Curve No. | — | 2 |

Detector: Dionex, Pulsed Electrochemical Detector
Detection mode: Integrated Amperometry

| Pulse voltage: | E1: +0.05 V (400 m sec), |
|---|---|
|  | E2: +0.75 V (200 m sec), |
|  | E3: −0.15 V (400 m sec) |

Flow rate: 1.0 ml/min
Range: 1 μC
Amount injected: 5 μl each of 0.1% aqueous solution injected
Cycle of analysis: 120 min
3) Results
In each chromatogram, the peak value is compared by the elution time. Each peak becomes high in order of the polymerization (molecular weight) according to the progress of retention time.

(Product of Firm C): There are about 40 peaks in the elution time between about 6.5 min and about 40 min. Most of the peaks occur in the elution time between 6.5 min and 14.5 min, indicating that the product is rich in polysaccharides of low polymerization.

(Product of Firm D): There were about 40 peaks in the elution time between about 14.5 min and about 46 min. This indicates that the product is rich in polysaccharides of relatively high polymerization.

(Product of Firm B): There were about 30 peaks in the elution time between about 7.9 min and about 30 min. Most of the peaks occur in the elution time of 14.5 min or more, but there is some peaks at less than 14.5 min, showing the presence of polysaccharides.

(Product of Firm A): There were about 40 peaks in the elution time between about 9 min and about 41 min. The shape of the peaks showed the same trend as that of Firm D, but a few peaks were found slightly in the elution time between 6.5 min and 14.5 min.

From these results and the respective catalogues, it is estimated that the peak at the retention time 6.5 min corresponds to the degree of polymerization of 2, and the peak at 14.5 min corresponds to 10.

EXAMPLE 2

(1) The Production Amount of IFT Enzyme and the Yield of DFA III from Inulin

Using 4 types of the above-mentioned commercial products, the enzymatic reaction was carried out with a fructosyltransferase as mentioned below to investigate the yield of DFA III. Inulin was completely dissolved in hot water at 80° C. and cooled down to 60° C. There was added IFT 5000 unit/kg inulin, and the mixture was allowed to react at 60° C. with stirring for 24 hours. The production amount of IFT enzyme in the reaction mixture was determined as follows. The reaction mixture was deactivated (at 80° C.), defecation through active carbon (Taiko Active Charcoal S) and filtered for diatomaceous earth (Radiolite 700), and the filtrated solution reaction mixture was applied to liquid chromatography (hereinafter referred to as HPLC; Shodex Sugar KS-801, 300×8 mm, I.D., flow rate 1 ml/min, column temperature 80° C.) to quantitatively analyze DFA III. Table 2 shows the production amount of IFT enzyme and the yield of DFA III.

As seen clearly from the results, Product of Firm D was best in the production amount of IFT enzyme and the yield of DFA III. From the results of FIG. 3 and Table 2, it was found that the products in which the higher degree of fructose polymerization is distributed (i.e., the polymerization degree of Products of Firms A and D is expected 10 or higher) afford DFA III of good yield. In this connection, inulin of higher molecular weight (polymerization degree) is poor in solubility and becomes difficult to handle, and accordingly, the upper limit of the polymerization degree of DFA III is approximately 100 in an industrial scale production.

(2) Determination of the Enzyme Productivity (Enzyme Activity)

In a 2 ml tube was placed 0.5 ml of 10% inulin solution and 0.45 ml of 0.1M citric acid/NaOH buffer (pH 5.5), and the mixture was warmed in a hot water bath at 60° C. for about 5 minutes. There was added 50 µl of a crude enzyme solution, and the mixture allowed to react at 60° C. for 10 min. The mixture was then kept in a boiling water for 5 minutes to quench the reaction. DFA III thus produced was determined by HPLC. The enzyme amount when it produced 1 µmole of DFA III for 1 minute was regarded as 1 unit.

TABLE 2

Yield of DFA III in the enzymatic reaction

| Kind of inulin | Enzyme Productivity (units/ml) | Yield of DFA III (%) |
|---|---|---|
| a) Firm A Product | 96.2 | 71.3 |
| b) Firm B Product | 80.3 | 57.8 |
| c) Firm C Product | 68.9 | 53.8 |
| d) Firm D Product | 102.4 | 76.5 |

EXAMPLE 3

Production of DFA III from Inulin (1) The product of Firm D (200 kg) is dissolved in 1000 kg of hot water at 80° C., and cooled down to 60° C. To the resulting solution is added IFT 5000 units/kg inulin (prepared in the production of an enzyme as shown below), and the mixture is stirred at 60° C. for 24 hours to yield a DFA III solution. The reaction mixture is heated up to 80° C. to deactivate the enzyme. To this deactivated solution is added Taiko Active Charcoal S (Futamura Kagaku Kogyo KK; average particle size 35 microns, less than 147 microns), and the mixture is stirred at 60° C. for 10 minutes. The mixture was then filtered through diatomaceous earth (Showa Chemical Ind.; Radiolite 700). That is, the above diatomaceous earth was pre-coated on the outside of a ceramic tube (Japan PALL KK.: PR-12 type ceramic tube), through which a solution containing active carbon was passed under increased pressure, and the filtrate was recovered inside the tube.

(2) The filtrate is concentrated in an evaporator (at 60-70° C., 120 mmHg or lower). The filtrate was concentrated to the final concentration R-Bx 77, and its mother liquor was moved to the crystallization step. Crystallization was conducted under cooling. The condensate at 60° C. is placed in a cooling vessel equipped with a cooling mantle and a stirrer, and cooled down to 15-20° C. over 23 hours. The mother liquor in which crystals precipitate is separated into crude crystals and syrup with a separator (3000 rpm, 1200 G). The crude crystals (DFA III purity 97%) are redissolved, and the resulting solution (DFA III purified solution) is treated in the same manner as above, i.e., treatment with active carbon, filtration through diatomaceous earth, concentration, crystallization and separation, to yield product crystals (DFA III purity 99%). The resulting crystals were dried under drafting at 50° C. to yield 7.2 kg of DFA III (moisture 0.1%). The crystals had no color and no smell.

(3) In the above operation (1), the filtration was carried out using a membrane filter (MF) in place of diatomaceous earth.

Figure 4:
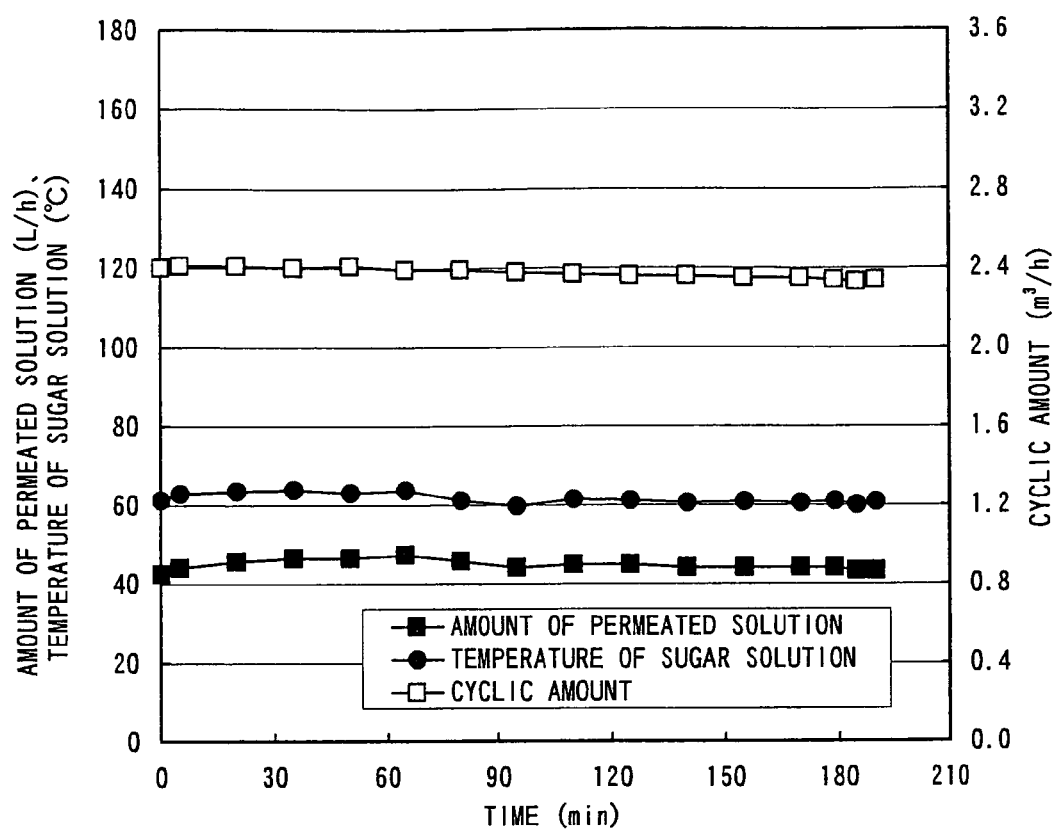
FIG. 4 shows the results of a filtration test by MF (membrane filter).

That is, the reaction mixture after completion of enzymatic reaction (approx. R-Bx20) is deactivated, to which Taiko Active Charcoal S is added at a rate of 1% per the solid portion, and the mixture is stirred at 60° C. for 10 minutes. This was filtered through a 0.14 µm membrane filter (Tsukishima Kikai Co., Ltd.; ceramic membrane TSK-TAMI Dahlia). The rate of concentration was set 10 fold. FIG. 4 shows the results. No decrease of the amount of the filtrate was recognized, and it was confirmed that filtration could be conducted smoothly. The filtrate was clear.

(4) In the above operations (1) and (2), a DFA III solution (a solution after completion of the enzymatic reaction; concentration R-Bx60, DFA III purity 78.6%, others 21.4% (mainly tetra-saccharides and penta-saccharide)) was chromatographed as follows to give the fractions as shown below (Table 3). Thus, 0.600-0.700 L/L-R of fractions as eluents were recovered and a DFA III fraction (purity 97.3%) was obtained. Thus, it was also confirmed that the DFA III fraction fractionated by chromatography can be subjected to filtration for defecation as a DFA III rich fraction and then to concentration, and the resulting condensate can be used as a mother liquor for crystallization or as a solution for redissolution of crude crystals (DFA III purification liquor) or additive thereto. It was also confirmed that the DFA III (purity 76.8%) fraction can be utilized as a DFA III non-rich fraction in the route C.

TABLE 3

| Fraction (L/L – R) | Purity (%) | Recovery (%) |
|---|---|---|
| 0.500-0.599 | 76.8 | 61.4 |
| 0.600-0.700 | 97.3 | 32.9 |

(Condition of Chromatography)
Chromatographic resin: Na type strongly acidic resin (Organo: CR-1310 type)
Column: 22×525 mm, 200 ml
Feeding Solution for Chromatography:
 DFA III containing solution for enzymatic reaction, which is deactivated and added with powdered active carbon for defecation and filtered.
 R-Bx 60, DFA III purity 78.6%
 Feeding amount 2.5% L/L-R
Elution condition: 70° C., SV=0.6 (2.0 ml/min)
Eluent: water
Fraction recovered: 5 ml/fraction

EXAMPLE 4

Production of Fractosyltransferase (1) *Arthrobacter* sp. AHU 1753 strain (FERM BP-8296) was incubated in the following condition to yield an enzyme solution.

(2) Culture medium 1: 1% glucose, 1% polypeptone, 0.5% yeast extract, 0.5% sodium chloride, pH 7.0. The culture medium (100 ml) was made in a 500 ml Sakaguchi shaking flask and sterilized with steam under pressure.

Culture medium 2: 1% inulin, 0.2% sodium nitrate, 0.05% sodium chloride, 0.05% magnesium sulfate, 0.05% potassium dihydrogen phosphate, 0.01 g/L ferric sulfate, 0.5% yeast extract, pH 7.0. The culture medium (100 L) was made in a 200 L jar fermenter (Hitachi Ltd.; Model FF-02) and sterilized with steam under pressure.

(3) Culture (Production of Enzyme)

Pre-culture: Aplatinum loop of *Arthrobacter* sp. AHU 1753 strain taken out from a stock slant was inoculated on Culture medium 1 under sterile condition. Incubation was conducted at 27° C. with shaking for 24 hours. Shaking condition: 15 cm stroke, 120 rpm.

Main Culture: The culture broth (1 L, 10 flasks, 1% pre-culture broth for the main culture broth) prepared in the pre-culture was inoculated on Culture medium 2 under sterile condition. The jar fermenter was operated at 27° C. for 17 hours. Aeration: 1 vvm (100 L/min); frequency of stirring: 300 rpm.

(4) Recover of the cells and others: The culture broth prepared in (3) was separated by a centrifuge into the cells and the supernatant (2000 G, 4° C., 20 minutes), and the latter was used as a DFA III enzyme solution. The enzyme solution was adjusted at pH 5.5 with phosphoric acid and stocked at −20° C.

(Results)

By the above operation, IFT could be produced.
Concentration: 300 units/ml (culture broth)(3 times as high as a laboratory level)
Total amount: $4.5 \times 10^7$ unit amount (sufficient amount corresponding to industrial scale production)
Time: 17 hours (shorter than that of a laboratory level)
(Condition of Culture)
Pre-culture: 27° C., 24 hours, shaking culture
Main culture: The pre-culture broth is inoculated on a main culture broth (1% pre-culture broth for the main culture broth) and incubated at 27° C. with shaking for 24 hours.
(Preparation of an Enzyme Solution)
The main culture broth is centrifuged (2000 G, 4° C., 20 minutes), and the supernatant is used as an enzyme solution.

EXAMPLE 5

Treatment with Yeast of a DFA III Containing Solution for Enzymatic Reaction Inulin (Product of Firm C) (200 kg) was dissolved in 1 kg of hot water at 80° C., to which IFT 5000 units/kg inulin was added, and the mixture was stirred at 60° C. for 12 hours to yield a DFA III solution.

This solution after the reaction completion was heated up to 80° C. to deactivate the enzyme, and after completion of deactivation, cooled down to 30° C. Subsequently, there was added yeast (Nippon Beet Sugar Manufacturing Co., Ltd.; Nitten Yeast)(100 g, moisture 66%), and the mixture was incubated at 30° C. under aeration for 12 hours.

The resulting yeast-treated solution was filtered (ceramic membrane, etc.), and the filtrate was concentrated to about Bx 50-70 and used as a feeding solution for chromatography.

EXAMPLE 6

Production of DFA III Granulates

Crystals of DFA III were finely pulverized with a mortar, to which water was added in an amount of 10 parts per 100 parts of DFA III, and the mixture was homogenized. This was granulated with an extrusion granulator (Fuji Powdal Co.; FINERYUZER, type EXR-60, performance 40-150 kg/hr) and dried at 70° C. with a blower-type thermostatic incubator (Yamato Science Co.; type DN910) for 3 hours to yield granular DFA III.

By 20 expert panelists, crystal DFA III; finely pulverized DFA III and granular DFA III were subjected to a sensory test. The results are shown in Table 4. As shown in Table 4, the finely pulverized DFA III had a stronger sweetness than the crystal DFA III and the former was improved in easiness of dissolution and sharpness of sweetness, affording a good result. The granular DFA III showed approximately the same sweetness as the finely pulverized DFA III, but the former was improved in easiness of dissolution in the mouth and sharpness of sweetness, and totally evaluated highly.

TABLE 4

Sensory test for the respectively processed DFA III

| Sweetness | Oral sense of dissolution | Sharpness of sweetness | Total evaluation |
|---|---|---|---|
| Evaluation of finely pulverized DFA III to crystal DFA III | | | |
| +1.2 | +1.4 | +0.5 | +1.7 |
| Evaluation of granular DFA III to evaluation of finely pulverized DFA III | | | |
| +0.1 | +0.5 | +0.2 | +0.5 |

Sweetness
+2: sweet
+1: slightly sweet
0: hard to answer
−1: less sweet
−2: not sweet
Sharpness of sweetness
+2: plain and simple
+1: somewhat plain and simple
0: hard to answer
−1: slightly over-rich
−2: over-rich
Oral sense of dissolution
+2: good
+1: slightly good
0: hard to answer
−1: slightly worse
−2: worse
Total evaluation
+2: good
+1: slightly good
0: hard to answer
−1: slightly worse
−2: worse From the above results, it was confirmed that the oral sense of dissolution and sharpness of the sweetness of crystal DFA III, which had been kept at a distance in an aspect of the taste or sense as food, were improved by finely pulverizing and further granulating them.

In this operation, the condition of crystallization was R-Bx: 65 or more, which corresponded to that of the crystallization of DFA III under cooling (judged from the solubility at 50° C.).

EXAMPLE 7

Large Scale Production of Fructosyltransferase (1) *Arthrobacter* sp. AHU 1753 strain (FERM BP-8296) was incubated in the following condition to yield an enzyme solution.

(2) <<Culture medium 1>>: 1% glucose, 1% polypeptone, 0.5% yeast extract, 0.5% sodium chloride, pH 7.0. The culture medium (100 ml) was made in a 500 ml Sakaguchi shaking flask and sterilized with steam under pressure.

<<Culture medium 2>>: 1% inulin, 0.2% sodium nitrate, 0.05% sodium chloride, 0.05% magnesium sulfate, 0.05% potassium dihydrogen phosphate, 0.01 g/L ferric sulfate, 0.5% yeast extract, pH 7.0. The culture medium (100 L) was made in a 200 L jar fermenter (Hitachi Ltd.; Model FF-02) and sterilized with steam under pressure.

(3) Culture (Production of Enzyme)

Pre-culture: A platinum loop of *Arthrobacter* sp. AHU 1753 strain taken out from a stock slant was inoculated on Culture medium 1 under sterile condition. Incubation was conducted at 27° C. with shaking for 24 hours. Shaking condition: 15 cm stroke, 120 rpm.

Main Culture: The culture broth (1 L, 10 flasks, 1% pre-culture broth for the main culture broth) prepared in the pre-culture was inoculated on Culture medium 2 under sterile condition. The jar fermenter was operated at 27° C. for 17 hours. Aeration: 1 vvm (150 L/min); frequency of stirring: 300 rpm.

(4) Recover of the cells and others: The culture broth prepared in (3) was separated by a centrifuge into the cells and the supernatant (2000 G, 4° C., 20 minutes), and the latter was used as a DFA III enzyme solution. The enzyme solution was adjusted at pH 5.5 with phosphoric acid and stocked at −20° C.

(Results)

By the above operation, IFT could be produced. Concentration: 300 units/ml (culture broth), (3 times as high as a laboratory level)

Total amount: $4.5 \times 10^7$ unit amount (sufficient amount corresponding to industrial scale production)

Time: 17 hours (shorter than that of a laboratory level)

(Condition of Culture)

Pre-culture: 27° C., 24 hours, shaking culture

Main culture: The pre-culture broth is inoculated on a main culture broth (1% pre-culture broth for the main culture broth) and incubated at 27° C. with shaking for 24 hours.

(Preparation of an Enzyme Solution)

The main culture broth is centrifuged (2000 G, 4° C., 20 minutes), and the supernatant is used as an enzyme solution.

EFFECTS OF THE INVENTION

The invention for the first time succeeded in industrially producing highly pure DFA III crystals which could not long be produced efficiently on an industrial scale. Further, according to the invention, highly purified DFA III crystals of which the purity reaches as high as 99 w/w % can be produced efficiently on an industrial scale by systematically combining particular treatment with active carbon and improvement of the purity of a DFA III containing solution. In addition, the invention succeeded for the first time in eliminating a smell existing in the crystals industrially and efficiently, which smell could not be eliminated in the prior art so far without repeating recrystallization many times. These are marked effects of the invention.

Thus, since the DFA III crystals of the invention have such a remarkable effect as they are highly pure and have no smell, they are particularly suitable in use for pharmaceuticals or food and drink. For example, they can optionally be used as calcium absorbents.

Accession Number: FERM BP-8296
Indication of Deposit: *Arthrobacter* sp. AHU 1753
Name of Depository Institution:
 International Patent Organism Depositary,
 National Institute of Advanced Industrial Science and Technology
Address of Depository Institution:
 AIST Tsukuba Central 6, 1-1, Higashi 1-chrome,
 Tsukuba-shi Ibaraki-ken, 305-8566 Japan
Date of Deposition: Feb. 18, 2003.

The invention claimed is:

1. A process for purifying difructose dianhydride III (DFA III) having a purity based on dry weight of at least 70% (w/w), comprising:
 contacting under aeration (i) a solution containing DFA III having a DFA III purity based on dry weight of at least 60% (w/w) and less than 70% (w/w) and having an R-Bx of 10 or more, with (ii) a yeast that acts on disaccharides or monosaccharides other than DFA III to degrade or incorporate said disaccharides or monosaccharides other than DFA III into the yeast, and with (iii) active carbon particles for a time and under conditions sufficient for impurities to adsorb on the active carbon particles, wherein said active carbon particles are added in amount of 5% (w/w) or less based on the dry weight of the DFA III containing solution, and wherein the activated carbon particles have an average particle size from 15 to 200 microns, thereby providing a contacted solution;
 separating the contacted solution into a solid phase and a liquid phase; and
 recovering from the liquid phase DFA III having a purity based on dry weight of at least 70% (w/w), thereby purifying DFA III.

2. The process of claim 1, wherein the recovering the DFA III having a purity of 70% (w/w) or more based on dry weight comprises separating the DFA III having a purity of 70% (w/w) or more based on dry weight chromatographically.

3. The process of claim 2, wherein the recovering comprises obtaining a chromatographically purified DFA III by chromatographically separating DFA III from the DFA III containing liquid phase or from the DFA III having a purity of at least 70% (w/w) based on dry weight.

4. The process of claim 1, comprising filtering the contacted solution thereby separating the solid and liquid phases.

5. The process of claim 1, wherein the recovering comprises crystallizing DFA III having a purity of at least 95% (w/w) based on dry weight from the DFA III having a purity based on dry weight of at least 70% (w/w), wherein said crystallized DFA III lacks the smell of DFA III crystals produced by a method not employing the active carbon particles.

6. The process of claim 1, wherein the recovering comprises crystallizing DFA III having a purity of at least 99% (w/w) based on dry weight from the DFA III having a purity based on dry weight of at least 70% (w/w), wherein said crystallized DFA III lacks the smell of DFA III crystals produced by a method not employing the active carbon particles.

7. The process of claim 1, wherein said DFA III containing solution is obtained by treating inulin with a fructosyltransferase, wherein the polymerization degree of fructose in said inulin is 10 or more.

8. The process of claim 1, wherein said DFA III containing solution is obtained by treating inulin with inulin fructotransferase, wherein the polymerization degree of fructose in said inulin is 10 or more.

9. The process of claim 1, wherein said DFA III containing solution is a solution produced by action of a fructosyltransferase on a fructose polymer or a material containing fructose polymer.

10. The process of claim 1, wherein said DFA III containing solution is a syrup suitable for crystallization and separation.

11. A process for producing difructose dianhydride III (DFA III) having a purity of at least 70% (w/w) based on dry weight, comprising:
producing a crude solution containing DFA III having a DFA III purity based on dry weight of less than 70% (w/w) but more than 60% (w/w) by contacting a DFA III containing solution with a yeast under conditions suitable for removing disaccharides other than DFA III and/or monosaccharides from the DFA III containing solution;
contacting the crude solution with 0.1% (w/w) to 5% (w/w), based on the dry weight of the DFA III containing solution, of activated carbon particles, wherein said particles have an average particle size from 15 to 200 microns, for a time and under conditions sufficient for impurities to adsorb on the activated carbon particles, thereby providing a contacted solution;
separating the contacted solution into a solid phase and a liquid phase; and
recovering from the liquid phase DFA III having a purity based on dry weight of at least 70% (w/w), thereby producing DFA III having a purity of at least 70% (w/w) based on dry weight.

12. The process of claim 11, wherein said crude solution is a DFA III containing fraction obtained by chromatographically removing said saccharides other than DFA III from the DFA III containing solution.

13. The process of claim 11, wherein the producing the crude solution further comprises defecating and filtering the DFA III containing solution.

14. The process of claim 11, wherein said crude solution has a concentration of R-Bx of 60 or more.

15. The process of claim 11, wherein the recovering further comprises recovering colorless and odorless DFA III crystals having a purity of at least 95% (w/w) based on dry weight.

16. A process for producing a purified difructose dianhydride III (DFA III) comprising:
providing a crude DFA III solution containing DFA III and impurities, said crude DFA III solution having a DFA III purity of at least 60% (w/w) based on dry weight;
adding to said crude DFA III solution up to 5% (w/w) of activated carbon particles, wherein said particles have an average particle size from 15 to 200 microns, for a time and under conditions sufficient for the impurities to adsorb onto the activated carbon particles thereby providing a treated crude DFA III solution;
separating the treated solution into a liquid phase and a solid phase; and
recovering from the liquid phase said purified DFA III as a purified DFA III solution.

17. The process of claim 16, wherein the crude DFA III solution is an extract obtained from Jerusalem artichoke, burdock, or chicory.

18. The process of claim 16, wherein the crude DFA III solution is produced by contacting a solution containing inulin with inulin hydrolase to produce DFA III and then deactivating the inulin hydrolase.

19. The process of claim 16, wherein the crude DFA III solution has an R-Bx of at least 60.

20. The process of claim 16, further comprising filtering the treated crude DFA III solution through diatomaceous earth and through a membrane filter prior to separating the liquid and solid phases.

21. The process of claim 16, further comprising concentrating the purified DFA III solution to form a liquid condensate, and then crystallizing the condensate, thereby obtaining a crystal or granule of said purified DFA III.

* * * * *